(12) United States Patent
Tyner

(10) Patent No.: US 8,066,237 B2
(45) Date of Patent: Nov. 29, 2011

(54) DEVICE FOR HOLDING PACKAGES

(75) Inventor: Jeffrey D. Tyner, Grand Rapids, MI (US)

(73) Assignee: CND Products LLC, Rockford, MI (US)

( * ) Notice: Subject to any disclaimer, the term of this patent is extended or adjusted under 35 U.S.C. 154(b) by 113 days.

(21) Appl. No.: 12/649,676

(22) Filed: Dec. 30, 2009

(65) Prior Publication Data

US 2011/0155870 A1  Jun. 30, 2011

(51) Int. Cl.
*F16M 11/00* (2006.01)

(52) U.S. Cl. ............... 248/201; 248/298.1; 248/905; 211/85.17

(58) Field of Classification Search .......... 248/905, 248/201, 298.1, 288.11, 300, 309.1, 311.2; 211/85.17, 85.15, 72, 85.18, 71.01
See application file for complete search history.

(56) References Cited

U.S. PATENT DOCUMENTS

| | | | | |
|---|---|---|---|---|
| 2,144,757 A | * | 1/1939 | Gilling et al. .......... | 242/596.1 |
| 4,022,415 A | * | 5/1977 | Roderick et al. ........ | 248/298.1 |
| 4,094,416 A | * | 6/1978 | Smith ..................... | 211/85.28 |
| 4,097,002 A | * | 6/1978 | Krueger .................. | 242/596.1 |
| 5,433,414 A | * | 7/1995 | Vieira ..................... | 248/316.4 |
| 5,662,288 A | * | 9/1997 | Chiang ................... | 242/596.8 |
| D437,167 S | * | 2/2001 | Hardaway ............... | D6/570 |
| 6,446,927 B1 | * | 9/2002 | Nuss ....................... | 248/309.2 |
| 6,755,382 B1 | * | 6/2004 | Melnick .................. | 248/316.8 |
| 7,278,544 B2 | * | 10/2007 | Blateri .................... | 211/85.15 |

* cited by examiner

*Primary Examiner* — Amy J. Sterling
(74) *Attorney, Agent, or Firm* — Warner Norcross & Judd LLP

(57) ABSTRACT

A device for holding a plurality of dispensing packages enables the packages to be independently removed and replaced. In one embodiment, the holding device includes a rear wall and a pair of sidewalls extending at an angle from said rear wall. The sidewalls each include a plurality of retaining elements, with each retaining element on one of said sidewalls being uniquely associated with a retaining element on the other sidewall. The rear wall of the holder may be selectively adjusted to vary the distance between opposing retaining elements. Each retaining element may separated from adjacent retaining elements so that each retaining element is independently flexible. Each retaining element may also include a retention hook that angles from the retaining element to hold a box behind the hook. The hook may additionally include a ramped surface that facilitates flexing of the retaining element as a box is inserted into the holder.

18 Claims, 6 Drawing Sheets

DEVICE FOR HOLDING PACKAGES

BACKGROUND OF THE INVENTION

The present invention relates to dispensing package holders, and, more particularly to a device for holding one or more boxes or packages that are designed for dispensing articles.

Devices for holding packages are particularly common in the medical services industry, for instance, for holding multiple boxes containing medical accessories. One specific example found in many hospital rooms is a device for holding multiple boxes of examination gloves, such as a box of small size gloves, a box of medium size gloves and a box of large size gloves. A common configuration of such a glove box holder includes a C-shaped receptacle with an opening at the upper end. Multiple boxes can be inserted through the opening so they are stacked on top of each other within the receptacle. The boxes are oriented within the receptacle such that the openings in the boxes face the gap in the C-shaped receptacle to allow users to remove gloves from the boxes through the gap.

Difficulties arise in the common glove box configuration when attempting to replace an empty glove box. All of the boxes in the receptacle above the empty box must be removed in order to access and remove the empty box. If the bottom box is empty, the top two boxes must therefore unnecessarily be removed in order to remove and replace the empty box. This often creates extra work for already overworked hospital staff members. In addition, removing and replacing boxes from a top-load style holder can be inconvenient for users, because of the need to reach over the top of the holder to remove each box. This can be particularly difficult for shorter users, or in situations where the holder must be mounted high on a support structure. Further problems arise because of the limited amount of available space in many environments, including hospital rooms. The space above the glove box holder may become cluttered with a variety of items, such as hoses or additional instruments, that can prevent easy removal of the packages from a top-loading holder.

SUMMARY OF THE INVENTION

The present invention provides a front loading device for holding a plurality of dispensing packages, such that the packages may be independently removed and replaced.

In one embodiment, the holding device includes a rear wall and a pair of sidewalls extending at an angle from said rear wall. The sidewalls each include a plurality of retaining elements, with each retaining element on one of said sidewalls being uniquely associated with a retaining element on the other sidewall. The rear wall may be selectively adjusted to vary the distance between the retaining elements on opposing sides of the sidewall. Various sizes of dispensing packages can be front loaded into the holder between the retaining elements and held in place by the retaining elements. The dispensing packages can also be independently removed from the holder by pulling the packages from between the retaining elements.

In one embodiment, each retaining element is separated from adjacent retaining elements so that each retaining element is independently flexible. For example, the sidewalls may include notches that separate the retaining elements from one another. Each retaining element may include a retention hook that angles from the retaining element to form a surface that can hold a box behind the hook. The hook may additionally include a ramped surface extending from the hook that facilitates flexing of the retaining elements as the boxes are inserted into the holder.

The holder may include a pair of bracket members that connect in a way that provides selective adjustability between the retaining elements. In one embodiment, both bracket members include a rear wall and a plurality of the retaining elements extending from the rear wall. The rear walls of the respective bracket members connect together to form the rear wall of the holder. The rear wall of one of the bracket members may include a slot, and the rear wall of the other bracket member may include a fastener hole that aligns with the slot so that a fastener can be inserted through the hole and tightened at various positions along the slot.

The present invention enables easy insertion and removal of individual dispensing packages from a single holder, without the need to remove or adjust any other packages in the holder.

DETAILED DESCRIPTION OF THE CURRENT EMBODIMENTS

I. Overview

Figure 1:
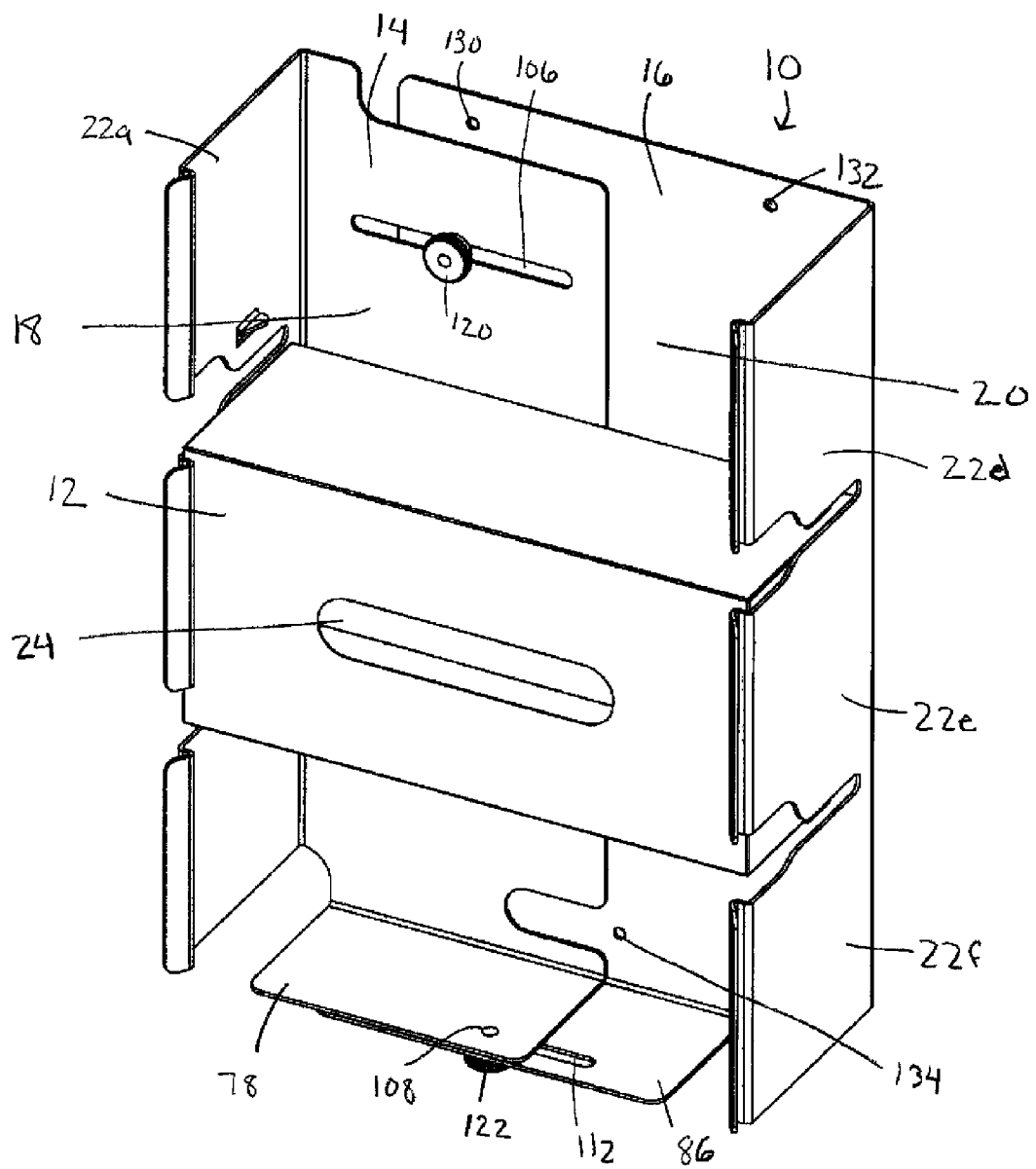
FIG. 1 is a front perspective view of a dispensing package holder according to one embodiment of the present invention, wherein a package is positioned in the holder.

A dispensing package holder according to one embodiment of the present invention is disclosed in FIG. 1 and generally designated 10. In the illustrated embodiment, the dispensing package holder is an apparatus designed to hold boxes 12, which may contain examination gloves. The present invention is not, however, limited to boxes or this particular type of box, and may otherwise be used or adapted for use with a wide variety of other types of dispensing packages, such as hair bonnet containers, shoe cover containers, and many others.

As shown, the holder 10 generally includes two bracket elements 14, 16 that each include a base portion 18, 20 and a plurality of retaining elements 22a-f extending outwardly from the base portions 18, 20 for retaining the boxes 12 within the holder. The holder 10 is designed such that each of the retaining elements 22 are independently flexible to enable a user to insert and remove one of the boxes 12 through the front of the holder 10 without interference from the other boxes 12. The bracket elements 14, 16 are connected in a way that enables the distance between the retaining elements 22 on one bracket 14 to be selectively adjusted with respect to the retaining elements 22 on the other bracket 16. This adjustability enables the holder 10 to be adjusted to accommodate boxes 12 and other packages of various widths.

II. Structure

As noted above, the glove boxes 12 are one of many different types of packages that may be held in the holder of the present invention. For purposes of illustration, the present invention will be shown and described in connection with the glove boxes 12. As shown, the glove boxes 12 are generally rectangular, with an oval shaped opening 24 on one side. The opening 24 may be initially covered, for instance, by a perforated cover, and removed when the contents of the box 12 need to be accessed. The contents, such as examination gloves, may be removed from the box 12 by pulling them through the opening 24.

The package holder 10 includes two bracket elements 14, 16. In one embodiment, the front bracket element 14 includes a base portion 18 having an upper edge 30, a lower edge 32, first and second side edges 34, 36, a front surface 38 and a rear surface 40. As shown, a sidewall 42 extends outwardly from the front surface 38 at the first side edge 34. In the illustrated embodiment, the sidewall 42 extends generally perpendicular to the base portion 18. The angle, as well as the position of the sidewall 42 on the base portion 18, could be varied from application to application. The sidewall 42 includes a base 44 adjacent the base portion 18 and a distal end 46 opposite the base 44. As shown, the sidewall 42 includes two notches 48, 50 extending into the sidewall 42 from the distal end 46, forming three separate retaining elements 22a, 22b and 22c. The notches 48, 50 enable each of the retaining elements 22a-c to flex independently of the other retaining elements. The degree of flexibility can be controlled by changing the depth and width of the notches. In the illustrated embodiment, the notches 48, 50 extend from the distal end 46 thorough substantially all of the sidewall 42, and they taper from an initial width near the distal end 46 of the sidewall 18 to a narrower width approaching the base 44. Although the illustrated embodiment includes two notches and three retaining elements 22, other embodiments may have only two retaining elements or more than three retaining elements.

In one embodiment, the rear bracket element 16 includes a base portion 20 having an upper edge 60, a lower edge 62, first and second side edges 64, 66, a front surface 68 and a rear surface 70. A sidewall 72 extends outwardly from the front surface 68. The retaining elements 22d-f extending from the rear bracket element 16 are essentially a mirror image of the retaining elements 22a-c extending from the front bracket element 14, and therefore will not be described again in detail. When the front 14 and rear 16 bracket elements are connected, each retaining element 22a-c on the front bracket element 14 is uniquely associated with one of the retaining elements 22d-f on the rear bracket element 16, such that they form coupled pairs of retaining elements 22. For example, retaining elements 22a and 22d form a first coupled pair of retaining elements, retaining elements 22b and 22e form a second coupled pair and retaining elements 22c and 22f form a third coupled pair. In the illustrated embodiment, the retaining elements of each coupled pair are generally aligned with each other when the front 14 and rear 16 bracket elements are connected. In another embodiment, the retaining elements may be offset from each other, or of different sizes such that a retaining element on one bracket element may have a different size or shape as its coupled pair. In yet another embodiment, only one of the two retaining elements in a coupled may be flexible. For instance, in one embodiment, only one of the two sidewalls 42, 72 may include notches 48, 50.

The package holder 10 may include ledges for supporting the boxes 12 at different heights and preventing the boxes 12 from interfering with each other as they are inserted or removed from the holder 10. In the illustrated embodiment, the front bracket element 14 includes three ledges 74, 76 and 78 for supporting boxes 12 at three different heights, with each height corresponding to the location of one of the coupled pairs of retaining elements 22. The upper ledge 74 is punched from the center of one of the retaining elements 22a, and bent inwardly from the retaining element 22a approximately perpendicular to the retaining element 22a. The ledge 74 is triangular in shape, having a width that increases towards the base 44 of the sidewall 42. The center ledge 76 is formed from a piece of material that extends from the lower edge 80 of the retaining element 22b. Like the ledge 74, the ledge 76 extends approximately perpendicular to the sidewall 42 and is triangular in shape. The bottom ledge 78 is a flange that extends outwardly from the lower edge 32 of the base portion 18 of the front bracket element 14. The ledge 78 is generally rectangular, and it extends from the base portion 18 approximately perpendicular to the base portion 18. In the illustrated embodiment, the ledge 78 extends the entire width of the base portion 18. In an alternative embodiment, any of the ledges 74, 76, and 78 may extend from either the sidewall 42 or from the base portion 18, and the size and shape of the ledges may vary from application to application. The rear bracket element 16 may also include three ledges 82, 84, and 86. In the illustrated embodiment, the upper ledge 82 and center ledge 84 on the rear bracket 16 extend outwardly from the lower edges 88, 90 of the retaining elements 22d and 22e respectively. As shown, the heights of the ledges 82 and 84 are offset from the corresponding ledges 74 and 76 on the front bracket element 14 to enable an upper box 12 to be seated on either ledge 74 or 82 and a central box 12 to be seated on ledge 76 or 84. This allows the holder 10 to accommodate boxes of varying heights. The lower ledge 86 on the rear bracket 16 extends from the lower edge 62 of the base portion 20 in the same manner as the lower ledge 78 on the front bracket 14.

Figure 5:
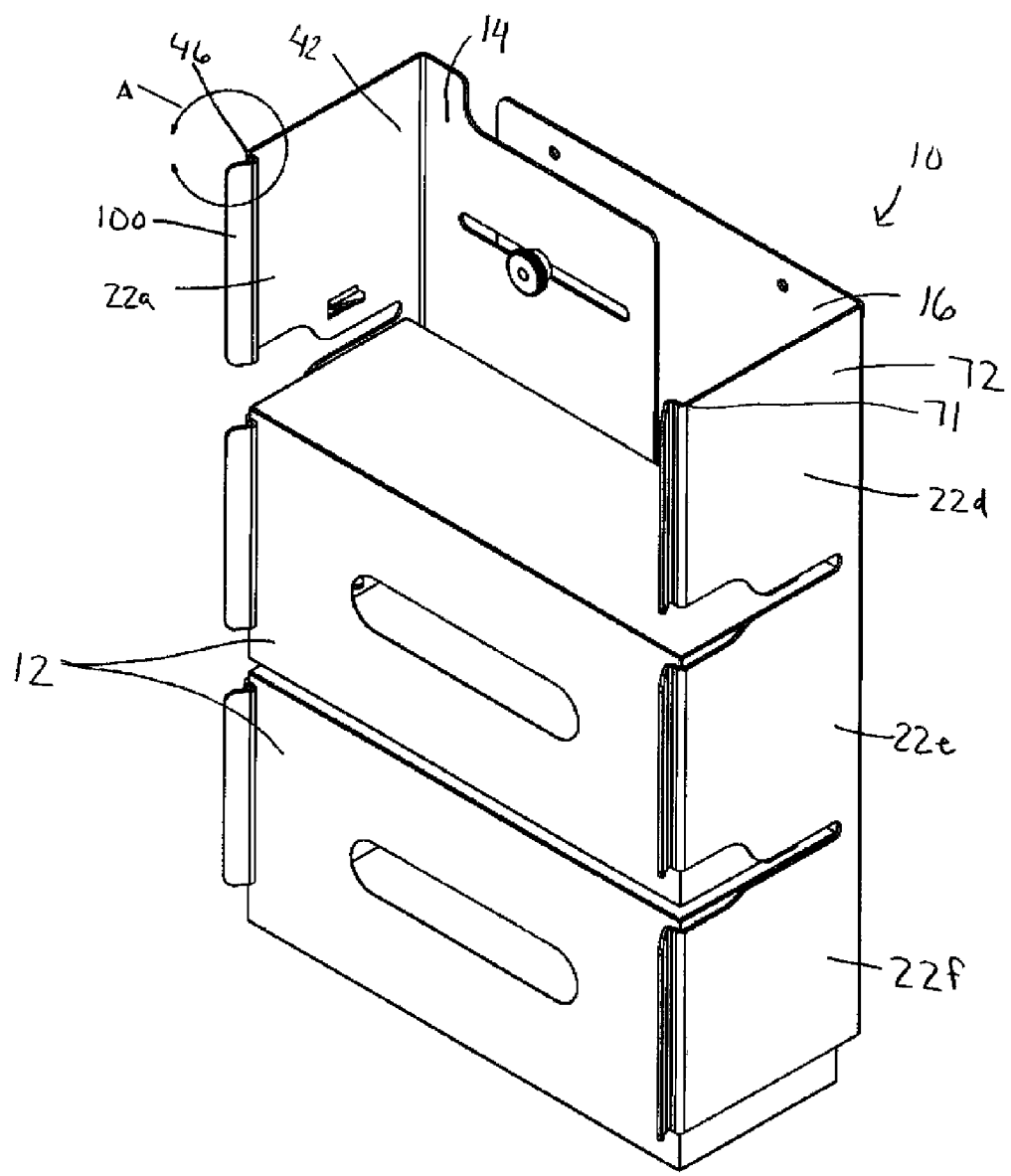
FIG. 5 is a front perspective view thereof with two packages positioned in the holder.
Figure 5A:
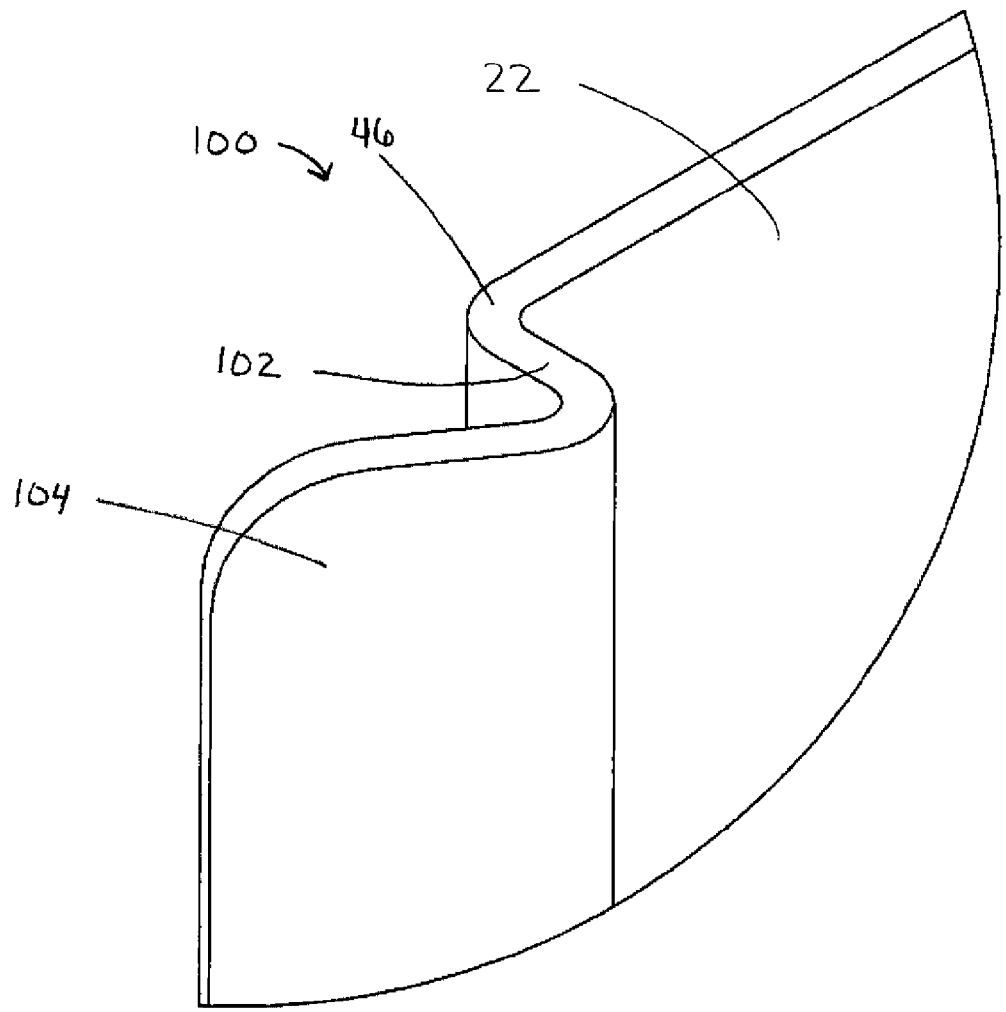
FIG. 5A is a close up view of the portion of the dispensing package holder in circle A in FIG. 5.

As shown in FIG. 5, and more particularly in FIG. 5A, each retaining element 22a-f may include a retainer hook 100. In one embodiment, the retainer hooks are shaped to facilitate flexing of the retaining members 22a-f when a box 12 is inserted between the retaining members 22a-f and to retain the boxes 12 behind the retainer hook 100 when they are inserted beyond the retainer hooks 100. In the illustrated embodiment, the retainer hooks extend from the distal end 46 of the sidewall 42 and the distal end 71 of the sidewall 72, and each retainer hook 100 includes a retention portion 102 extending inwardly toward the opposing sidewall and a flex portion 104 extending at an angle from the retention portion 102. As shown, the retention portion 102 extends from the retaining element 22a-f at an angle approximately perpendicular to the retaining element 22a-f and the flex portion 104 extends from the retention portion 102 such that it is angled outwardly (i.e. away from the opposing sidewall). In this way, the retention portion 102 forms a ramped surface that, when engaged by a box 12, will flex the retaining element 22a-f outwardly to allow the box 12 to pass beyond the retaining hook 100. In an alternative embodiment, the retaining hooks may have another shape. For instance, the retaining hooks may include only the retention portion 102. Optionally, the holder may not include retaining hooks 100, and may retain the boxes in another manner, such as the frictional resistance of the retaining elements 22a-f on the sides of the boxes 12.

Figure 2:
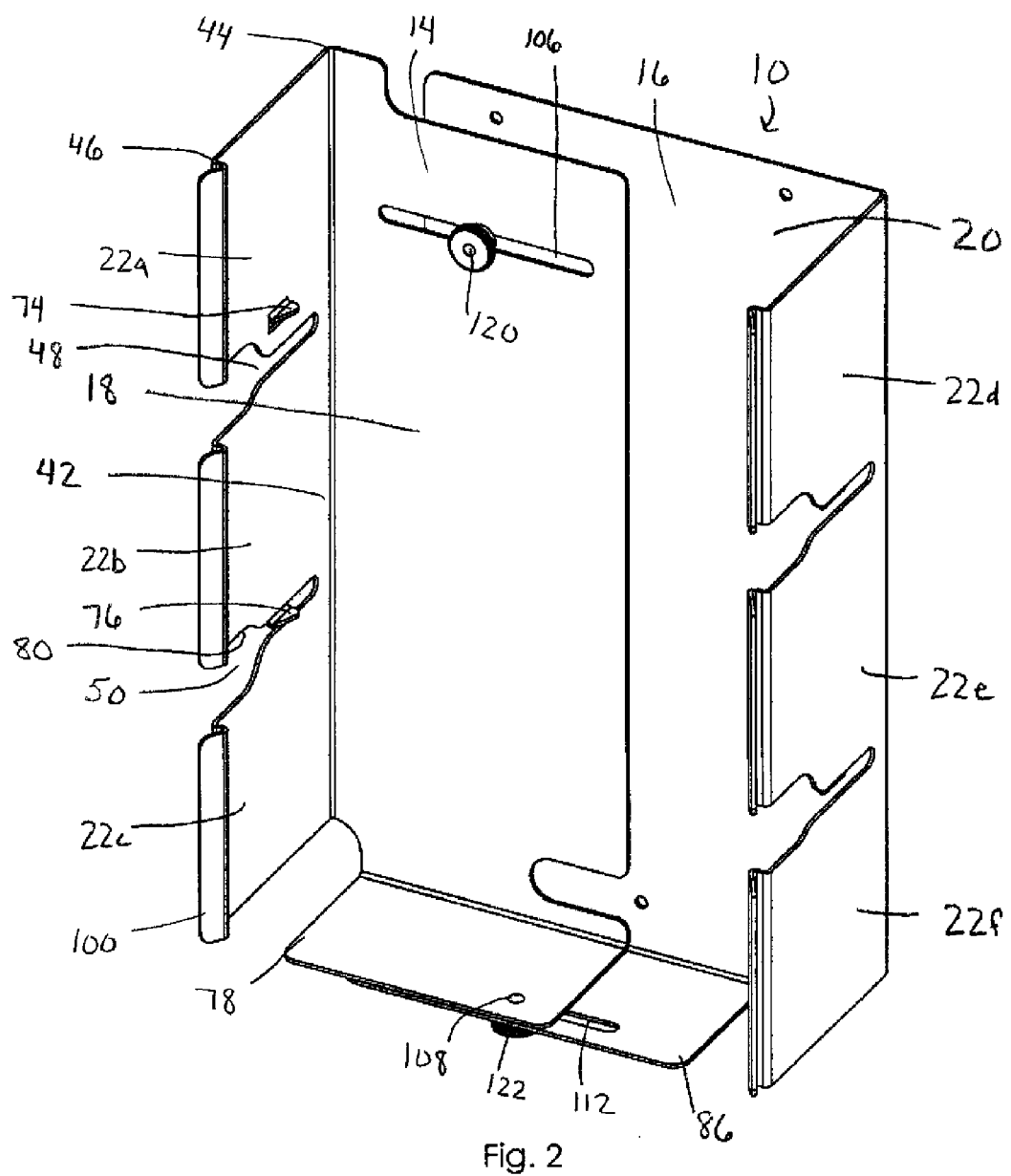
FIG. 2 is a front perspective view thereof with no packages in the holder.
Figure 3:
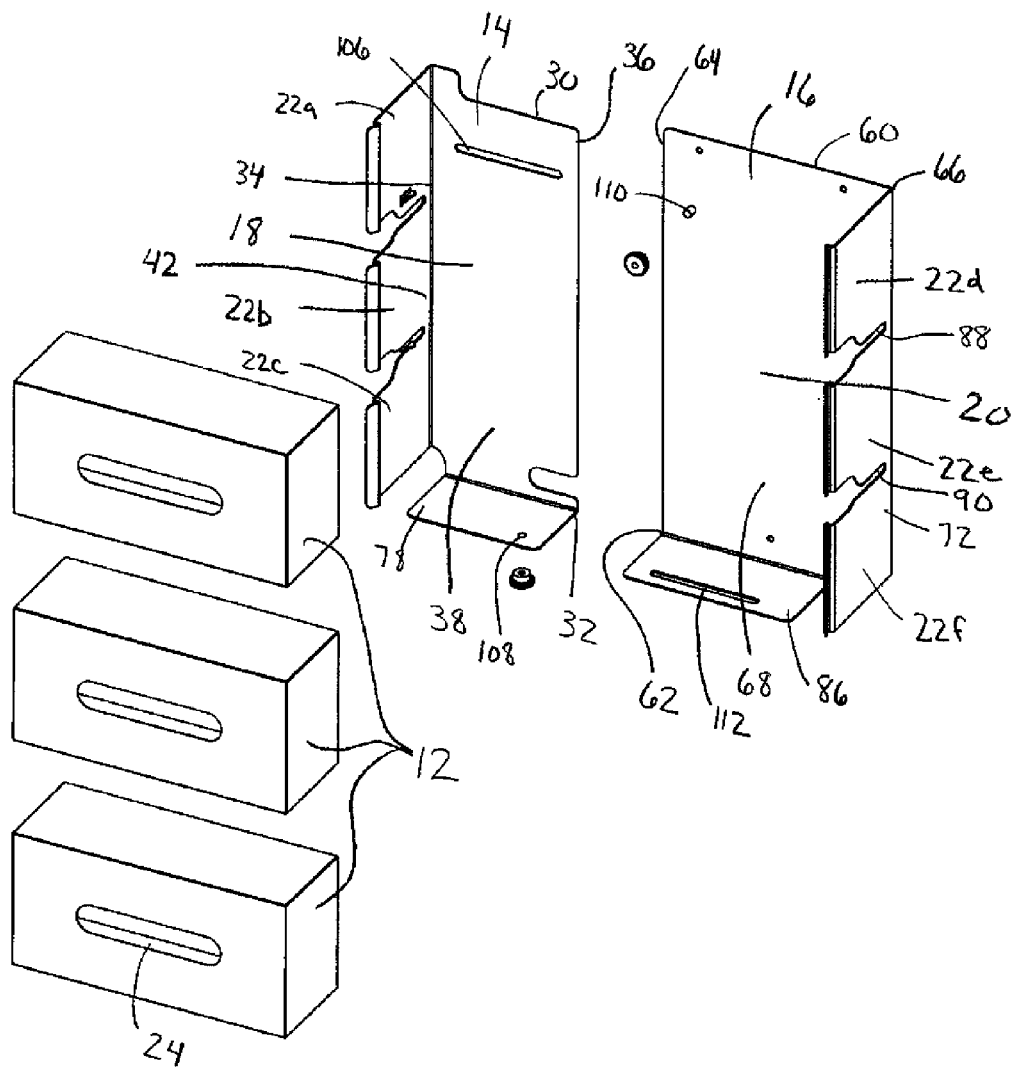
FIG. 3 is an exploded view thereof.
Figure 4:
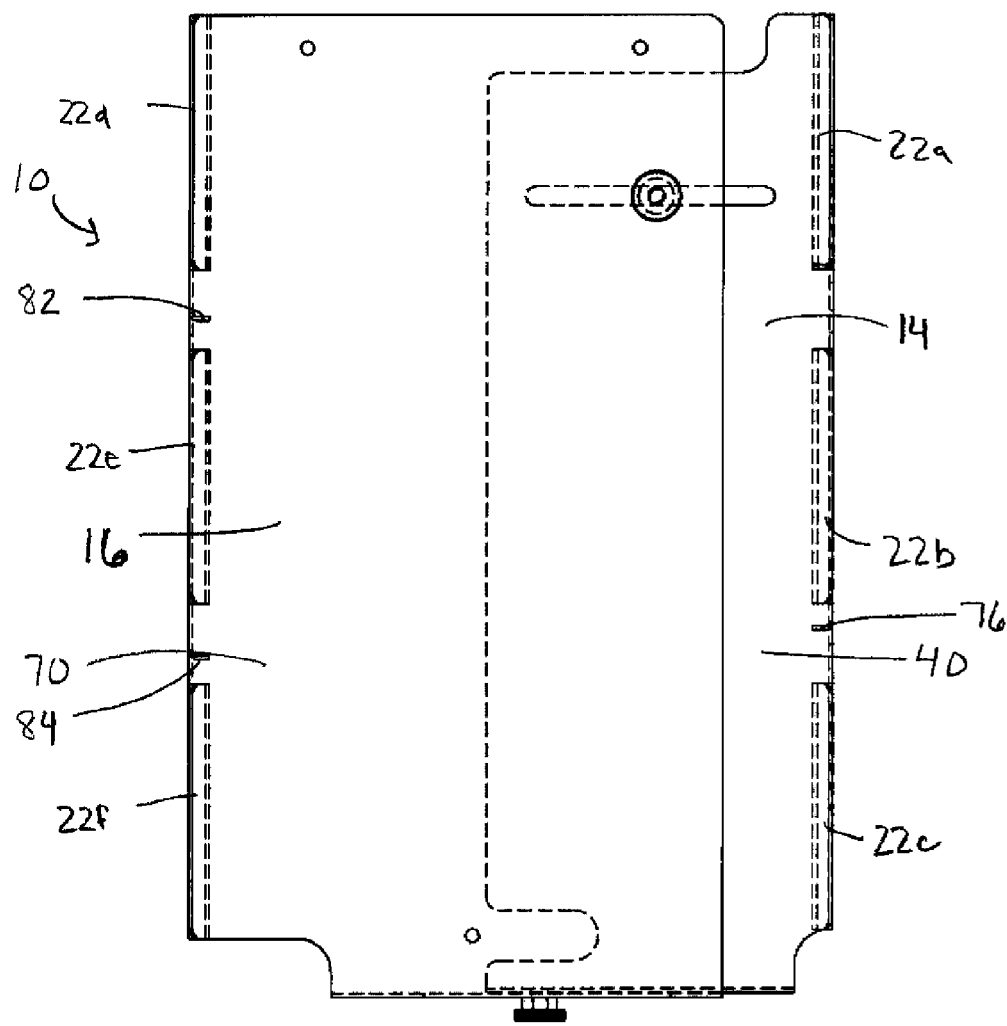
FIG. 4 is a rear view thereof.

The front 14 and rear 16 bracket elements are connected together in a way that allows the distance between the coupled pairs of retaining elements 22a-f to be selectively adjusted to accommodate for boxes of varying widths. In the illustrated embodiment, the front bracket member 14 includes an elongated slot 106 extending across the base portion 18 and a fastener hole 108 on the lower ledge 78, and the rear bracket member 16 includes a fastener boss 110 extending from the base portion 20 and an elongated slot 112 extending across the lower ledge 86. As shown in FIG. 2, the slot 106 is positioned to align with the fastener boss 110 and the slot 112 is positioned to align with the fastener hole 108 when the front bracket member 14 is positioned in front of the rear bracket member 16 such that fasteners 120, 122 can extend through the aligned slots and holes to secure the front 14 and rear 16 bracket members together. The fasteners 120, 122 may be repositioned within the slots 106, 112 to selectively adjust the position of the front bracket portion 14 with respect to the rear bracket portion 16 and the distance between opposing retaining elements 22*a-f*. In the illustrated embodiment, the fasteners 120, 122 each include screw portion (not shown) and a knob 124 that enables a user to easily loosen and tighten the screw portion of the fasteners 120, 122 to easily adjust the distance between the retaining elements 22*a-f*. A variety of alternative embodiments may be used to enable the selective adjustability of the front and rear brackets 14, 16. For example, the slots 106, 112 may be replaced with a series of holes, or the slots may be eliminated and the fasteners may be configured to tighten directly against the front surface 68 of the rear bracket 16.

In addition, the front 14 or rear 16 brackets may include structure for mounting the holder 10 to a support structure, such as a wall or a rail mounting system. As illustrated, the rear bracket portion 16 includes three mounting holes 130, 132, 134 that receive fasteners for mounting the rear bracket portion 16, and thus the holder 10, to a wall. In another embodiment, the holes may be repositioned to attach to a particular rail structure. Other methods for mounting the holder 10 to a support structure, such as hooks on the rear surface 70 of the rear bracket 16.

III. Operation

Operation of the illustrated embodiment generally includes mounting the rear bracket member 16 to a support structure using the fastener holes 130, 132, 134 by extending conventional fasteners (not shown) through the holes and into the support structure, or into a clip that attaches to the support structure. Of course, in an embodiment with mounting structure on the front bracket 14, the front bracket may be mounted to the support structure in addition to or instead of the rear bracket. The front bracket member 14 is attached to the rear bracket member 16 by extending the fastener 120 through the slot 106 and the fastener boss 110 and the fastener 122 through the slot 112 and the fastener hole 108. At that point, a box 12 that is intended to be held in the holder 10 is positioned between one of the coupled pairs of retaining members 22*a-f* and the distance between the retaining members 22 in the coupled pair is adjusted by sliding the front 14 and rear 16 brackets with respect to each other via the slots 106 and 112 until the retaining members of the coupled pair contact, or nearly contact, the box 12 and the retainer hooks 100 are positioned in front of a portion of the box 12 to retain the box 12 behind the hooks 100. The fasteners 120, 122 are then secured by tightening the screws 120, 122 to keep the brackets 14, 16 in the desired position. In one embodiment, a the holder 10 is adjusted to the proper position by first inserting a box 12 into the bottom position of the holder, between retaining elements 22*c* and 22*f* and then moving the front 14 and rear 16 brackets until the retention hooks 100 are positioned in front of the box 12. The lower fastener 122 is then tightened to secure the brackets 14, 16 in that position. After assuring that the remaining retainer elements are properly aligned, the upper fastener 120 is tightened and additional boxes 12 are inserted into the upper positions. Of course, the order in which boxes 12 are inserted and fasteners are tightened may vary.

When the brackets 14, 16 are in the desired position, the holder 10 is ready for use. Boxes 12 may be inserted between coupled pairs of the retaining elements 22*a-f* until they are retained behind the retainer hooks 100 and supported by one or more ledges 74, 76, 78 or 82, 84, or 86. In the illustrated embodiment, as a box 12 is brought into contact with the flex portion 104 of a retainer hook 100, the ramped surface of the flex portion 104 is forced outwardly, causing the retaining element 22*a-f* corresponding to that retainer hook 100 to flex outwardly, independent from the other retaining elements 22*a-f*, until the box 12 has been inserted past the retention portion 102 of the retainer hook 100. Also in the illustrated embodiment, with ledges on opposing sidewalls 42, 72 that are offset in height from each other, each box 12 may be vertically supported by only one ledge. The particular ledge is selected by the user based on the height of the box 12. If a ledge on the opposing side of the holder 10 interferes with the box 12, the triangle shape of the ledge may help to deform the box 12 or even puncture the box 12 to allow the box 12 to fit in the selected position. Boxes 12 can be individually removed from the holder 10 by flexing one or both of the retaining elements in a corresponding pair outwardly to enable the box 12 to be pulled from behind the retention hook 100.

The above description is that of the current embodiments of the invention. Various alterations and changes can be made without departing from the spirit and broader aspects of the invention as defined in the appended claims, which are to be interpreted in accordance with the principles of patent law including the doctrine of equivalents. Any reference to claim elements in the singular, for example, using the articles "a," "an," "the" or "said," is not to be construed as limiting the element to the singular.

The invention claimed is:

1. An apparatus for supporting a plurality of dispensing packages, comprising:
   a first support element having a first base portion, a plurality of first retainers extending from said base portion, and a plurality of first ledges extending from said first support element;
   a second support element having a second base portion, a plurality of second retainers extending from said second base portion, and a plurality of second ledges extending from said second support element; and
   a fastener connecting said first and second support elements to each other such that the distance between said first retainers and said second retainers is selectively adjustable to a desired dimension corresponding to a dimension of the dispensing packages, wherein each of said first ledges is aligned with an associated one of said second ledges to form spaced apart pairs of said first and second ledges, wherein the dispensing packages can be inserted between said first and said second retainers with each individual dispensing package supported on one of said pairs of first and second ledges.

2. The apparatus of claim 1 wherein said first support element includes a first flange extending from said first base portion, said first retainers extending from said first flange, wherein said second support element includes a second flange extending from said second base portion, said second retainers extending from said second flange.

3. The apparatus of claim 2 wherein first retainers are spaced from each other such that each said first retainer is independently flexible with respect to the other said first retainers.

4. The apparatus of claim 3 wherein said second retainers are spaced apart from each other such that each said second retainer is independently flexible with respect to the other said second retainers.

5. The apparatus of claim 4 wherein said first retainers each include a hook element extending from a respective one of said first retainers and said second retainers each include a hook element extending from a respective one of said second retainers, said hook elements each including an inwardly extending first portion capable of retaining of one of the dispensing packages behind said first portion.

6. The apparatus of claim 5 wherein said hook elements each include an outwardly extending second portion extending from said first portion, said second portion forming a ramped outer surface.

7. The apparatus of claim 6 wherein one of said first base portion and said second base portion defines a slot and the other of said first base portion and said second base portion defines a hole, said fastener extending through said slot and said hole.

8. The apparatus of claim 7 wherein one of said first base portion and said second base portion includes means for mounting the apparatus to a support structure.

9. An apparatus for holding a plurality of dispensing packages comprising:
  a bracket having a rear wall and a pair of sidewalls extending at an angle from said rear wall, said sidewalls each including a plurality of retainers, wherein each said retainer on one of said sidewalls is uniquely associated with one of said retainers on the other of said sidewalls to form cooperating pairs of retainers, each cooperating pair capable of retaining a dispensing package between said cooperating pair and said rear wall; and
  means for selectively adjusting the distance between said sidewalls, wherein said rear wall includes a first portion and a second portion, wherein said means for selectively adjusting the distance between said sidewalls includes selectively adjusting the position of said first portion with respect to said second portion.

10. An apparatus for holding a plurality of dispensing packages comprising:
  a bracket having a rear wall and a pair of sidewalls extending at an angle from said rear wall, said sidewalls each including a plurality of retainers, wherein each said retainer on one of said sidewalls is uniquely associated with one of said retainers on the other of said sidewalls to form cooperating pairs of retainers, each cooperating pair capable of retaining a dispensing package between said cooperating pair and said rear wall; and
  means for selectively adjusting the distance between said sidewalls, wherein at least one of said sidewalls defines a plurality of notches, each said notch separating one of said retainers from another one of said retainers such that each retainer is independently flexible.

11. The apparatus of claim 10 wherein each said sidewall includes a plurality of ledges extending inwardly therefrom, with each said ledge uniquely associated with one said retainer.

12. The apparatus of claim 11 wherein said ledges are formed unitarily with said sidewalls and are bent inwardly from said sidewalls.

13. The apparatus of claim 11 wherein said rear wall includes a first portion and a second portion, wherein said means for selectively adjusting the distance between said sidewalls includes selectively adjusting the position of said first portion with respect to said second portion.

14. The apparatus of claim 13 wherein one of said first portion and said second portion defines an elongated slot and the other of said first portion and said second portion defines a hole, said hole capable of being selectively adjusted with respect to said slot by a fastener extending through said hole and said slot.

15. The apparatus of claim 14 wherein one of said first portion and said second portion defines mounting holes for mounting the apparatus to a support structure.

16. The apparatus of claim 15 wherein said first portion and said second portion each include a bottom edge, and a bottom flange extending outwardly from said bottom edge.

17. The apparatus of claim 16 wherein one of said first portion bottom flange and said second portion bottom flange defines a slot, and the other of said first portion bottom flange and said second portion bottom flange defines a hole, said hole aligned with said slot such that a fastener can extend through said hole and said slot.

18. An apparatus for supporting a plurality of dispensing packages, comprising:
  a first bracket having a bottom edge and a top edge, said first bracket including a rear wall and a sidewall extending at an angle from said rear wall, said first bracket including a plurality of ledges spaced apart between said bottom edge and said top edge, said sidewall including a plurality of independently flexible portions, each said flexible portion including a retainer hook extending therefrom;
  a second bracket having a bottom edge and a top edge, said second bracket including a rear wall and a sidewall extending at an angle from said rear wall, said second bracket including a plurality of ledges spaced apart between said second bracket bottom edge and said second bracket top edge, said second bracket sidewall including a plurality of independently flexible portions, each said flexible portion on said second bracket including a retainer hook extending therefrom, wherein each said flexible portion on said first bracket is uniquely associated with one of said flexible portions on said second bracket to form coupled pairs of flexible portions;
  wherein one of said first bracket rear wall and said second bracket rear wall defines an elongated slot, and the other of said first bracket rear wall and said second bracket rear wall defines a hole, said hole aligned with said slot such that said first and second brackets are capable of being secured together by a fastener extending through said hole and said slot, said hole being selectively adjustable with respect to said slot, such that said first bracket sidewall and said second bracket sidewall can be spaced apart at a desired distance;
  wherein one of the dispenser packages can be retained between each of said coupled pairs of said flexible portions behind said retainer hooks of said first bracket and said second bracket.

\* \* \* \* \*